United States Patent [19]

Sichler et al.

[11] Patent Number: 5,516,288
[45] Date of Patent: May 14, 1996

[54] DEVICE AND METHOD FOR ATTACHING A MEMBER IN REPLACEMENT OF PART OF A SET OF TEETH

[75] Inventors: Heimo Sichler, Graz, Austria; Hans M. de Nieuport, Bergen op Zoom, Netherlands

[73] Assignee: Accius B.V., Bergen op Zoom, Netherlands

[21] Appl. No.: 976,976
[22] PCT Filed: May 29, 1991
[86] PCT No.: PCT/NL91/00087
§ 371 Date: Jun. 21, 1993
§ 102(e) Date: Jun. 21, 1993
[87] PCT Pub. No.: WO92/02191
PCT Pub. Date: Feb. 20, 1992

[30] Foreign Application Priority Data

Aug. 1, 1990 [AT] Austria ..................................... 1618/90

[51] Int. Cl.$^6$ ...................................................... A61C 8/00
[52] U.S. Cl. ................................................................ 433/173
[58] Field of Search ................................... 433/172, 173, 433/174, 175, 176, 177

[56] References Cited

U.S. PATENT DOCUMENTS

| | | | |
|---|---|---|---|
| 4,468,201 | 8/1984 | Fukuyo | 433/176 X |
| 4,609,354 | 9/1986 | Koch | 433/173 |
| 5,007,835 | 4/1991 | Valen | 433/174 |
| 5,178,539 | 1/1993 | Peltier et al. | 433/173 |
| 5,195,891 | 3/1993 | Sulc | 433/173 |
| 5,219,287 | 6/1993 | Nishihara | 433/173 X |
| 5,302,125 | 4/1994 | Kowanacki et al. | 433/173 X |
| 5,312,255 | 5/1994 | Bauer | 433/173 X |

FOREIGN PATENT DOCUMENTS

| | | |
|---|---|---|
| 0263274A1 | 8/1987 | European Pat. Off. . |
| 0158333A3 | 10/1986 | Germany . |

OTHER PUBLICATIONS

European (International) Search Report.

Primary Examiner—Nicholas D. Lucchesi
Attorney, Agent, or Firm—Peter L. Michaelson

[57] ABSTRACT

A device for attaching a member that replaces a part of a set of teeth, wherein the device has a pin to be implanted in a jawbone and a coupling pin with a ball-and-socket joint disposed between the coupling pin and the implantation pin. The ball and/or the socket of the joint is made of a memory material. The memory position is such that at body temperature pivotal motion of the ball-and-socket joint can simply be brought into a desired position. Thus, the coupling pin can be brought into any desired position, virtually independently of the orientation of the implantation pin in the jaw, so that the dental-replacement member can be fitted readily without any tension arising therein.

20 Claims, 8 Drawing Sheets

DEVICE AND METHOD FOR ATTACHING A MEMBER IN REPLACEMENT OF PART OF A SET OF TEETH

BACKGROUND OF THE INVENTION

1. Field of the Invention

The invention relates to a device for attaching a member in replacement of part of a set of teeth, comprising: a hollow pin to be implanted in jawbone and a coupling pin to be rigidly attached to the implantation pin by means of a ball-and-socket joint.

2. Descripton of the Prior Art

Such a device is disclosed in the European Patent Application 0,263,274. It is designed for anchoring in the mouth of, for instance, a human being, a dental-replacement member such as a crown, bridge or prosthesis in replacement of one or more teeth and/or molars.

A dental-replacement member is applied by first implanting one or more hollow pins in the patient's jawbone. After a certain time, the coupling pin for coupling the dental-replacement member is attached thereto. The exact position where such an implantation pin is implanted, as well as the orientation of the implantation pin relative to the bone, mainly depends on the constitution of the bone in question: it will be clear that it is desirable for the implantation pin to be implanted in a bone portion that satisfies certain minimum requirements with respect to thickness and solidity. It may thus happen that the orientation of the implantation pin relative to the bone deviates from the desired orientation relative to the dental-replacement member.

Particularly when a plurality of implantation pins are used to attach one and the same dental-replacement member, it is desirable for the coupling pins of these implantation pins to be oriented parallel to each other. However, in practice it is almost impossible to attach the implantation pins in parallel orientation: some degree of non-parallellism is nearly always inevitable.

Therefore, in order to facilitate the placing of the dental-replacement member onto the pins, and/or to allow for the setting of the orientation of the dental-replacement member with respect to the implantation pin, the coupling pin is attached to the implantation pin by means of a ball-socket joint. When orienting the coupling pin with respect to the implantation pin, the ball-socket joint is loosened; when the desired orientation is achieved, the ball-socket joint is secured.

In the known device, the ball-socket joint is an ordinary ball-socket joint which in itself provides only the orientation facility but not the fixation, while the above-mentioned securing of the ball-socket joint is achieved by the provision of securing means in the form of a clamping screw. Consequently, it is necessary to provide for some passage so that a tool can reach the clamping screw. Further, in the known device the socket of the ball-socket joint is necessarily made in two-part form, the two parts being screwed together. In order to let the socket receive the ball, said two socket parts need to be screwed loose, and after placing the ball in one socket part, the other socket part, which is shaped as a housing, must be placed over the ball and screwed to the first socket part.

One disadvantage of this known device is that it is constructionally complicated, in that it comprises two screw connections: one screw connection for the socket housing to the other socket part, and another screw connection for the securing screw.

SUMMARY OF THE INVENTION

Another disadvantage of this known device is that the securing force is applied locally, i.e. at the tip of the securing screw and at the rim of the socket housing, so that it is difficult to have the ball and the socket screwed tightly together without causing them to break.

A further disadvantage of this known device is that the socket housing needs to have a rather smooth outer surface, so that it is relatively difficult to get a good grip thereon for screwing it onto the other socket part without causing any damage like burrs.

It is an object of the invention to improve this known device.

More particularly, it is an object of the invention to provide a device for attaching a dental-replacement member, which permits stepless adjustment of the orientation of the pins protruding from the jaw, even after implantation, if so desired, but not at the expense of rigidity.

Further, it is an object of the invention to provide a device for attaching a dental-replacement member, which has a simple construction and is readily attachable.

Still further, it is an object of the invention to provide a device for attaching a dental-replacement member, wherein the loosening and securing of the ball-socket joint does not involve turning a screw.

To that effect, the device of the type described hereinabove is characterized according to the invention in that at least one of the coupling members of the ball-and-socket joint is at least partly made of a memory material.

The memory material is provided in the ball-and-socket joint in such a way that at the operating temperature thereof there is a tendency towards a memory position, with the result that a clamping force arises which fixes the ball-and-socket joint. Beyond a certain critical temperature, this effect does not occur and the memory material can be deformed to make the ball-and-socket joint freely movable, whereafter the ball-and-socket joint can be brought into any desired position, which desired position is fixed by adjusting the ball-and-socket joint to an operating temperature again.

BRIEF DESCRIPTION OF THE DRAWINGS

The invention will hereinafter be further explained, by way of example, by a description of preferred embodiments, with reference to the accompanying drawings, in which.

DETAILED DESCRIPTION OF THE PREFERRED EMBODIMENT

Figure 8:
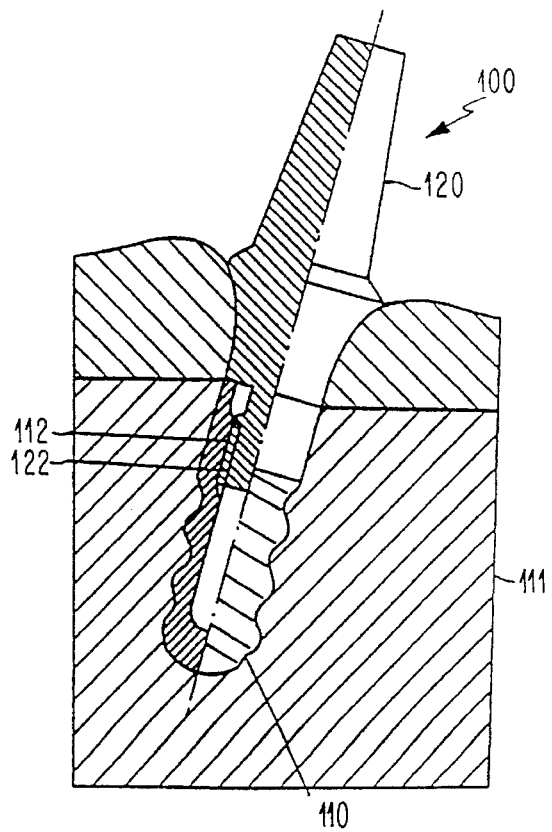
FIG. 8 schematically shows an elevational view of a known device for attaching a dental-replacement member.

First, reference is made to FIG. 8, showing a known device 100 for attaching a dental-replacement member. The device 100 comprises an in, plantation pin 110 to be implanted in jawbone 111, the terminal end of pin 110 being provided with an internally threaded portion 112. Screwed into this portion 112 is a corresponding externally threaded portion 122 of a coupling pin 120 to be coupled with a dental-replacement member (not shown). This figure clearly shows that the coupling pin 120 is disposed axially in alignment with the implantation pin 110, so that when the implantation pin 110 is implanted obliquely in the jawbone 111, the coupling pin 120 is also oriented obliquely relative to the jawbone 111.

Figure 1:
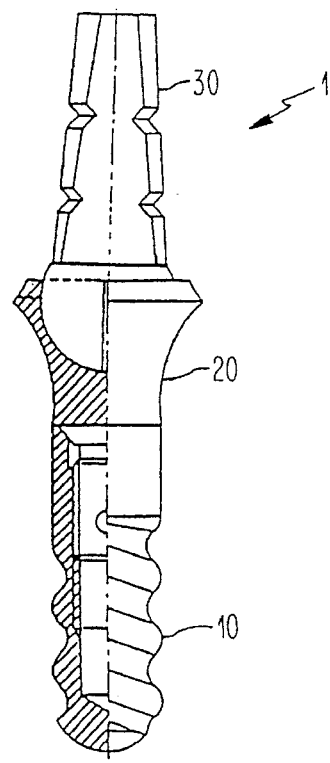
FIG. 1 shows an elevation, partly sectional, of one embodiment of a device according to the invention for attaching a dental-replacement member.
Figure 7A:
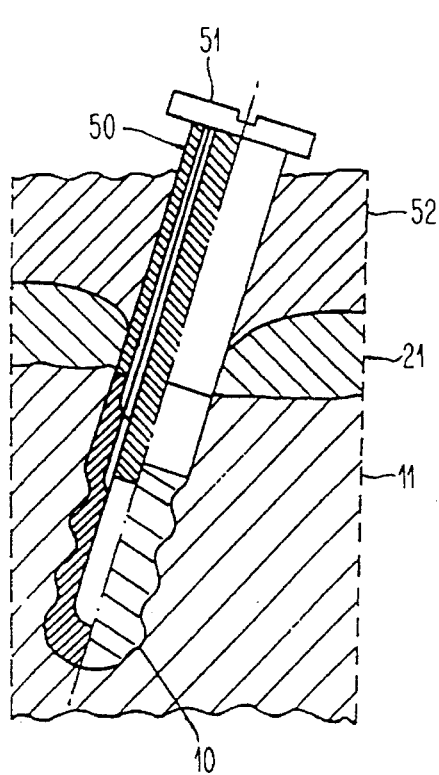
FIG. 7 schematically shows steps of setting a combination of a device according to the invention.
Figure 2A:
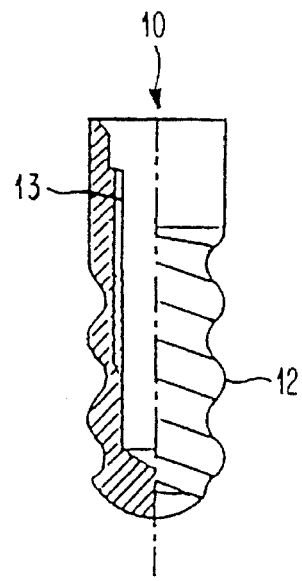
FIGS. 2A–2D shows elevational views, partly sectional, of the separate parts of the embodiment shown in FIG. 1.
Figure 2B:
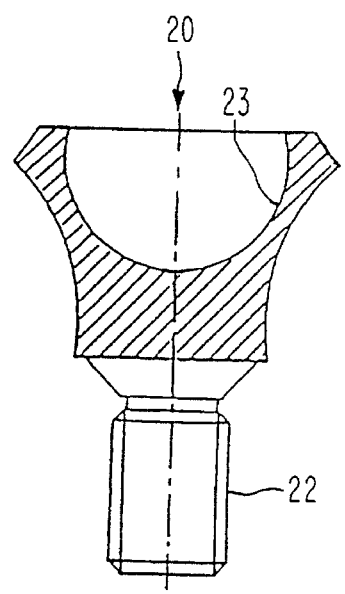
Figure 2C:
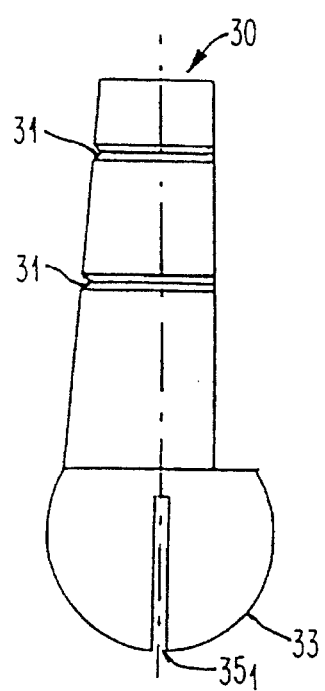
Figure 2D:
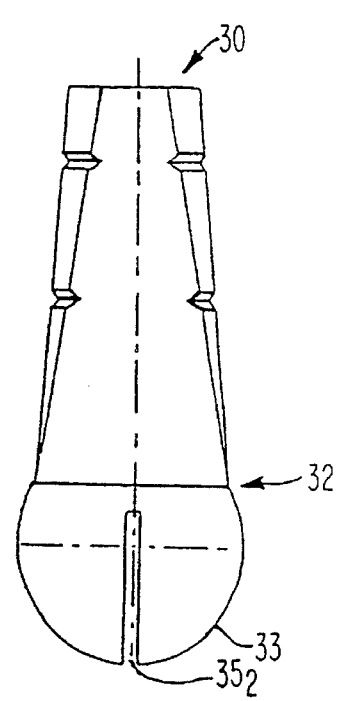

FIG. 1 shows a preferred embodiment of a device 1 according to the invention in assembled condition, while FIGS. 2A–2D separately shows the separate parts of this preferred embodiment: an implantation pin 10, a transmucosal member 20 and a coupling pin 30, which last is shown twice in FIGS. 2A, i.e. two mutually perpendicular side elevational views. The implantation pin 10 is intended for implantation in jawbone 11 (FIG. 3), and for that purpose is made of a material suitable for implantation, for instance titanium (grade 2) or $TiAl_4V_6$ (grade 5), and at its external surface is provided with a screw thread 12. Generally, the implantation pin 10 is provided externally with a coating of artificial bone, for instance calcium hydroxyl apatite. Generally, the implantation pin 10 has a hollow cylindrical form which is also provided internally with a thread 13, and is open at one end for receiving a correspondingly threaded portion 22 of the transmucosal member 20.

The function of the transmucosal part 20 is to bridge the layer of gums 21 (FIG. 3) on the jawbone 11 and for that purpose it is made of a suitable material therefor, such as $TiAl_4V_6$.

The coupling pin 30 is intended for coupling with a dental-replacement member 40 (FIG. 3), and for that purpose has a generally slightly tapering cylindrical shape, in which there may be provided circumferential grooves 31 whose function will be further explained. As will appear more in particular from the side elevation of FIGS. 2A–2D, the coupling pin 30 may be flattened on one side in the longitudinal direction, which is advantageous in particular when a member in replacement of a tooth is being attached, since a tooth has relatively small transverse dimensions and is somewhat concave on the inside, while, further, rotation of the dental-replacement member is prevented by virtue of the flattened portion and the corresponding recess in the dental-replacement member.

At its wider end 32, the coupling pin 30 is provided with a fixing portion 33 which is substantially shaped as a segment of a sphere. The purpose of spherical fixing portion 33 is to affix the coupling pin 30 in its operating position to the transmucosal member 20 at the operating temperature, which member 20 is provided for that purpose with a corresponding spherical hollow 23. During the setting of the coupling pin 30 relative to the implantation pin 10, the spherical fixing portion 33 and the corresponding spherical hollow 23 function as a ball-and-socket joint.

Figure 5A:
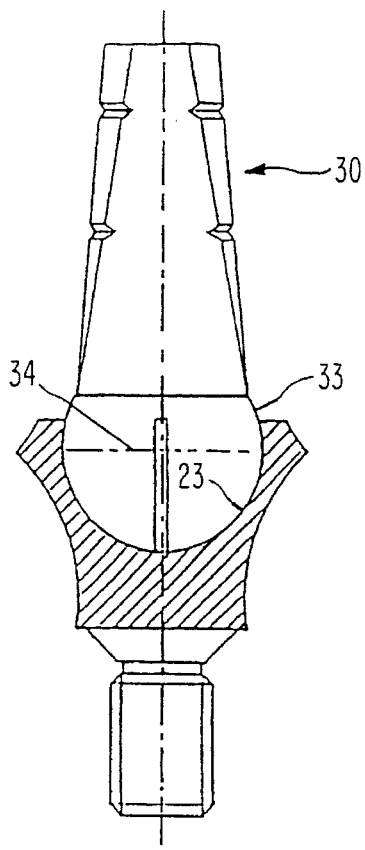
FIGS. 5A and 5B show further details of the embodiment shown in FIG. 1.
Figure 5B:
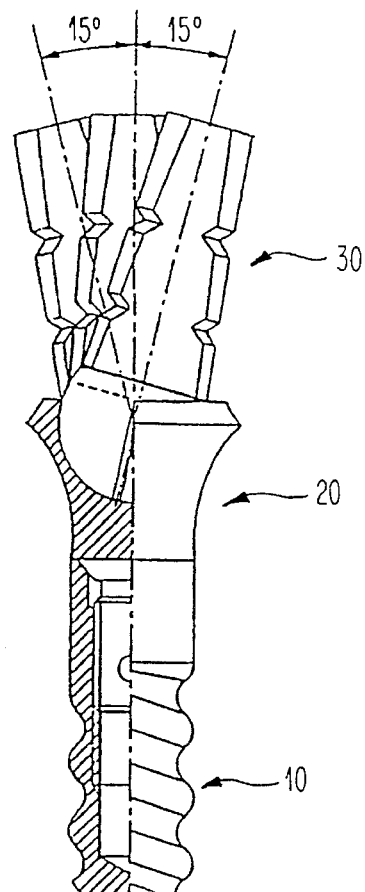

As shown in more detail in FIG. 5A, both the fixing portion 33 and the hollow 23 corresponding therewith extend beyond the diameter 34 of the spherical body, so that once the fixing portion 33 is disposed in the hollow 23, it can in principle be removed therefrom only by deforming at least one of the abovementioned parts, which will generally require considerable force. Further, the fixing portion 33 extends beyond the hollow 23, so that the longitudinal axis of the coupling pin 30 and the longitudinal axis of the implantation pin 10 can be displaced relative to each other through a certain angle, for instance at least 15°, as is illustrated more particularly in FIG. 5B. Further, it will be clear that the coupling pin 30 can be rotated 360° about its longitudinal axis relative to the implantation pin 10, and that the longitudinal axis of the coupling pin 30, displaced through the abovementioned angle relative to the longitudinal axis of the implantation pin 10, can be displaced through 360° relative to the longitudinal axis of the implantation pin 10 through a precessional movement.

The fixing portion 33 is divided into at least two parts 36 by at least one axially extending slot 35. Preferably, and as shown, there are provided two of such slots $35_1$ and $35_2$, perpendicular to each other, so as to divide the fixing portion 33 into four substantially equal quarters 36. The provision of more slots somewhat reduces the strength of the spherical portion 33; if only one slot is provided to divide the spherical portion 33 into two sphere parts, there is a chance that this will not permit sufficiently smooth adjustment. It is also possible, for instance, to provide three slots extending from the side only as far as the centreline to thereby divide the spherical portion 33 into three sphere parts, but this is more complicated from the point of view of manufacturing technique, and hence more expensive.

Figure 6A:
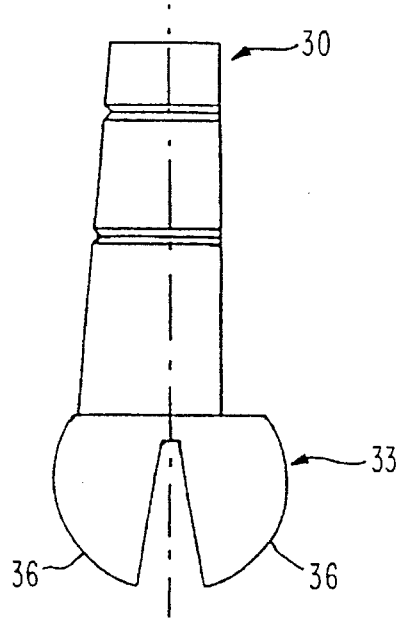
FIGS. 6A–6B shows a part of the embodiment shown in FIG. 1 in the memory position.
Figure 6B:
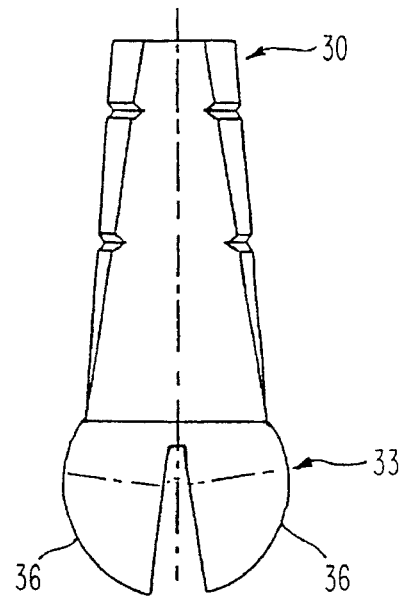

The fixing portion 33, at least the part thereof where the quarters 36 are joined together, consists of a memory material, with the parts 36 being disposed relatively far apart in the memory position (see FIGS. 6A–6B). The memory material is of such a type that the memory properties of the material in question are achieved at least in a temperature range that includes the normal body temperature of the carrier, which is about 37° C. in the human body. Normal operating temperatures in the mouth of the human body will not go beyond the range of 0° C. to 80° C. As in the memory materials known to date the memory effect occurs above a certain critical temperature, preferably a memory material is used with a critical temperature that is sufficiently lower than 37° C. and preferably about 0° C. A suitable material is known under the name of nitinol.

It is observed that although within the framework of the present invention it is possible for only a part of the coupling pin 30 to consist of memory material, for instance the spherical portion 33, while the remaining portion may consist of a different, cheaper material, it is easier from the point of view of manufacturing technique to make the entire coupling pin 30 of memory material.

Figure 3:
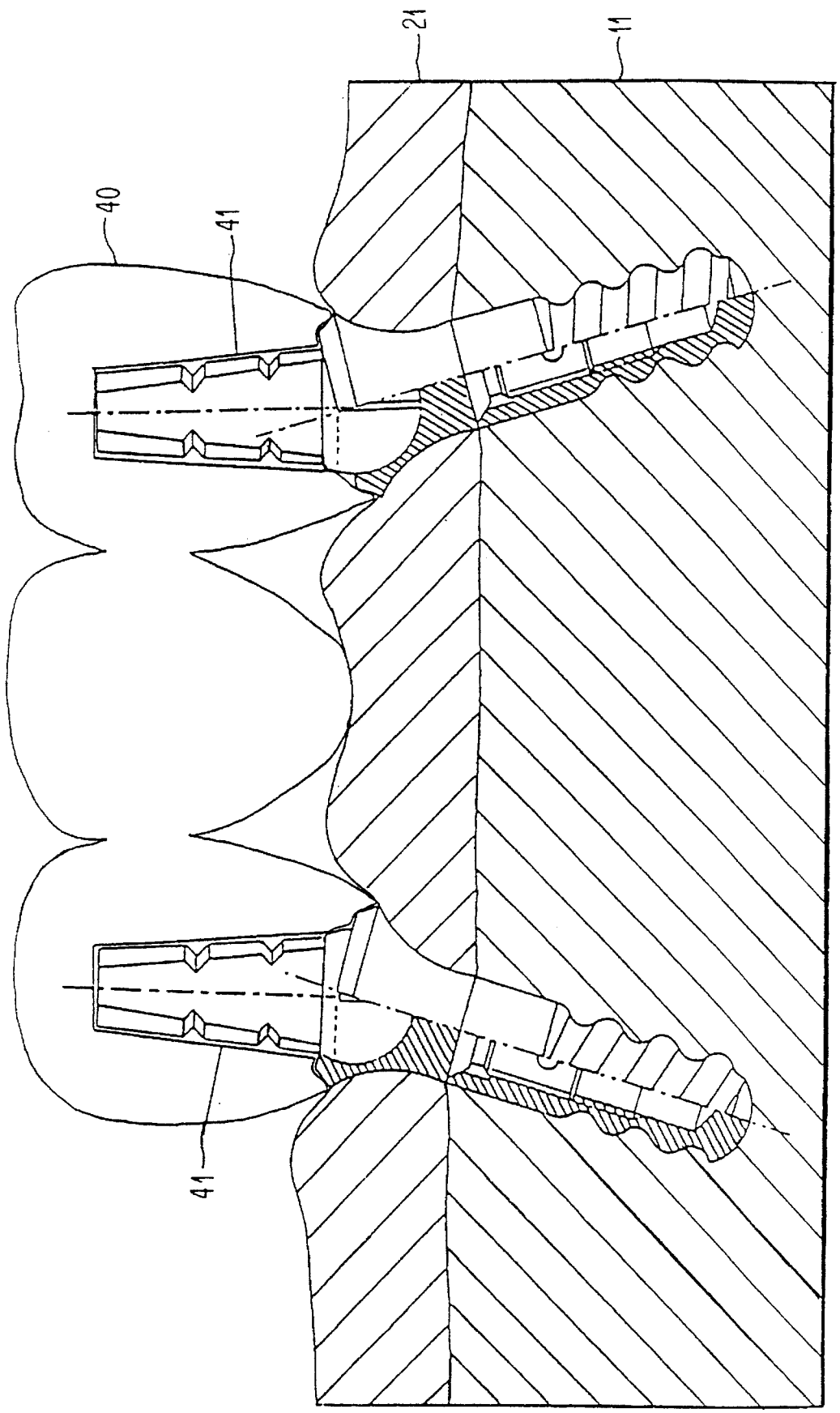
FIG. 3 schematically shows an example of an application of the embodiment shown in FIG. 1.

With reference to FIG. 3, now the attachment of a dental-replacement member 40 using a device 1 according to the invention will be described. For the sake of clarity, adjacent dental elements are not shown.

In a first session—that is, obviously, after any original dental elements and/or root parts have been removed, and, if so desired, a hole has been provided in the jawbone 11 —an implantation pin 10 is screwed into the jawbone 11, whereby the orientation of the implantation pin 10 is not critical.

In the practical example shown in FIG. 3, two of such implantation pins 10 have been implanted.

Figure 4A:
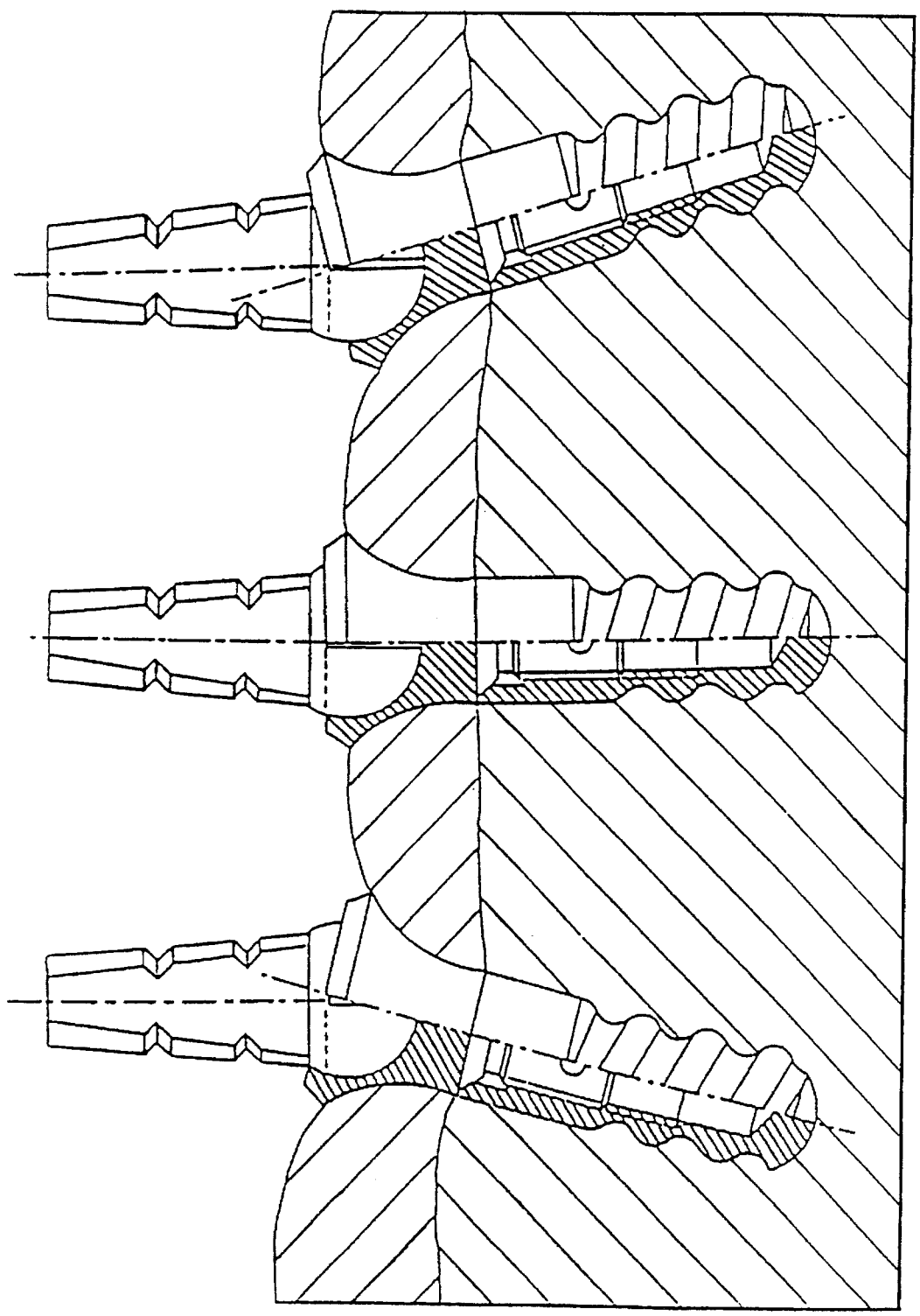
FIGS. 4A and 4B show other examples of applications of the embodiment shown in FIG. 1.
Figure 4B:
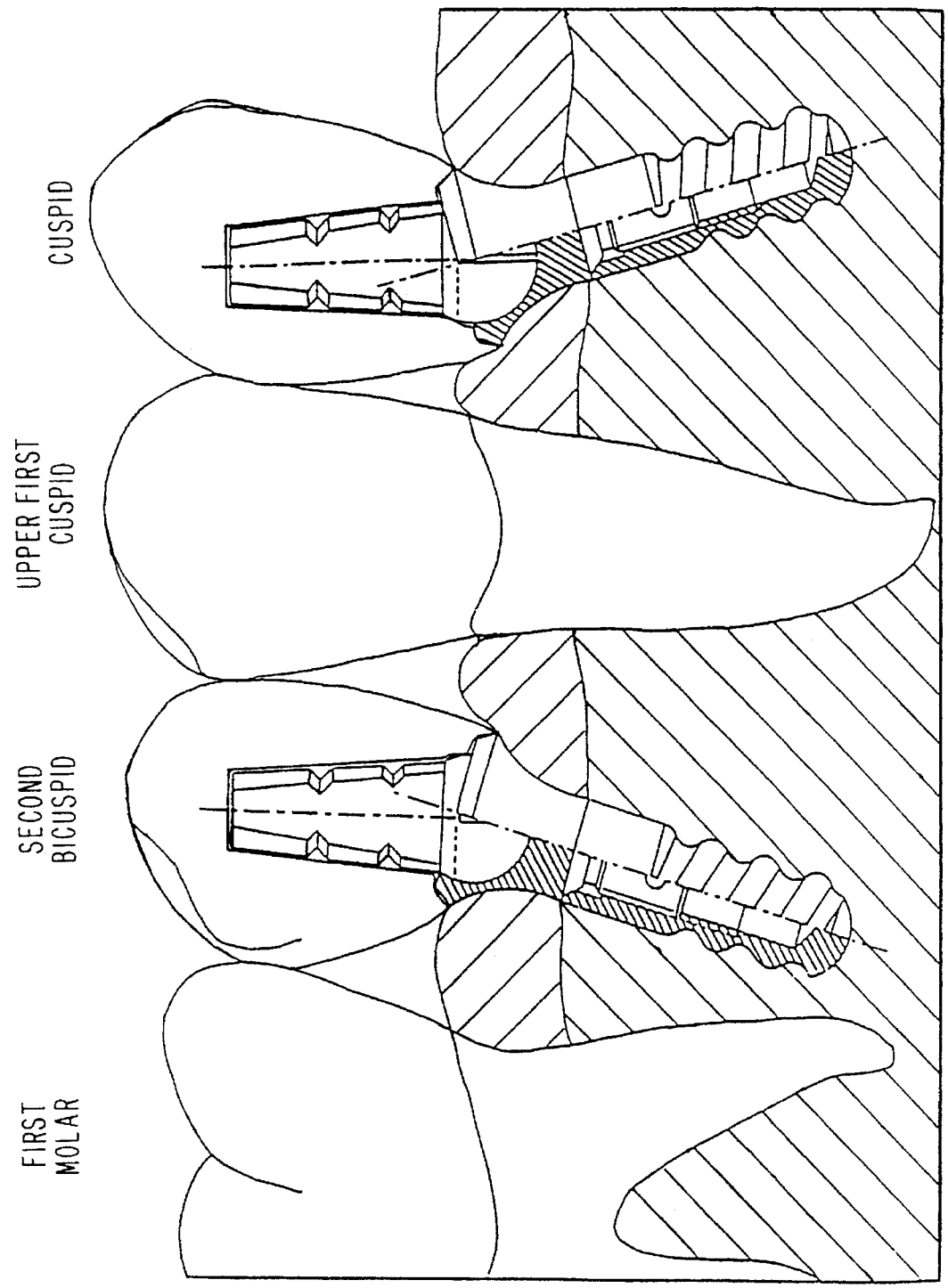

After the implantation pin 10 has sufficiently grown into the jawbone 11, i.e. that growth of the jawbone 11 has led to sufficient anchoring of the implantation pin 10, the combination of the transmucosal member 20 and the coupling pin 30 is screwed into the implantation pin 10. Preferably, each coupling pin 30 is positioned relative to the corresponding transmucosal member 20 in such a way, that after the screwing step each coupling pin 30 has a desired orientation relative to the jawbone 11. FIG. 3 shows that the two coupling pins 30 are oriented parallel to each other, in spite of the fact that the corresponding implantation pins 10 deviate considerably from this orientation. FIG. 4A shows a practical example in which three devices 1 according to the invention have been employed, with the three coupling pins 30 being oriented parallel to each other. FIG. 4B shows a practical example in which a device 1 is used for attaching separate dental elements.

After the gums have healed sufficiently, the dental-replacement member 40 can be mounted on the coupling pin(s) 30 by fitting the dental-replacement member 40 over the coupling pin(s) 30. For that purpose, the dental-replacement member 40 is provided with recesses 41 corresponding with the coupling pins 30. Securement of the dental-replacement member 40 relative to the coupling pin 30 can be accomplished by a click-fit connection, by depositing cement in the recesses 41 or by screwing one or more securing nuts (not shown for the sake of simplicity) in the dental-replacement member 40, which securing nuts extend into said circumferential grooves 31. This last possibility is particularly advantageous in the case of a comprehensive dental-replacement member 40, such as a bridge, in that, if so desired, the member 40 can be removed and re-placed again in simple manner without risk of damage, while the dental-replacement member 40 is still prevented from being "loose" in use.

It is noted that in general the manufacturer supplies to the dentist or dental surgeon the combination of coupling pin 30 and transmucosal member 20 as an assembly. The manufacture of such a combination can advantageously be realized in the following manner. Using means that are known per se, a transmucosal member 20 is manufactured from a suitable material, for instance $TiAl_4V_6$, with the transmucosal member 20 being provided, among other things, with a spherical recess 23, as described above. Likewise using known means, a coupling pin 30 is manufactured in its entirety from a memory material, for instance nitinol, with a critical temperature of about 0° C., the coupling pin 30 being provided, among other things, with a spherical fixing portion 33. The dimensions of the spherical fixing portion 33 are substantially equal to, possibly slightly smaller than, the dimensions of the spherical recess 23. In the spherical fixing portion 33 two axial slots 35 are provided to divide the spherical fixing portion 33 into four quarters 36, as described above. Using a suitable tool, these quarters 36 are moved apart at a temperature above the critical temperature until the position shown in FIGS. 6A–6B has been reached, where the external dimensions of the spherical fixing portion 33 are greater than the corresponding dimensions of the spherical recess 23.

This position shown in FIGS. 6A–6B is the so-called memory position of the spherical fixing portion 33. This means that at a temperature above the critical temperature, the spherical fixing portion 33 will at all times attempt to assume the position shown in FIG. 6A–6B. At a temperature below the critical temperature, this effect does not occur. This is made use of in the manufacture of the abovementioned combination by cooling the spherical fixing portion 33 to a temperature below the critical temperature and pinching the quarters 36 inwardly, whereby a plastics deformation can occur, and then introducing the spherical fixing portion 33 into the spherical recess 23 of the transmucosal member 20. In this condition the spherical fixing portion 33 is freely movable within the spherical recess 23, and the combination of the spherical fixing portion 33 and the spherical recess 23 functions as a ball-and-socket joint. In this condition, therefore, the coupling pin 30 can be brought into a desired orientation relative to the transmucosal member 20.

Then the temperature of the spherical fixing portion 33 is raised above the critical temperature. Under the influence of the memory effect, the quarters 36 will attempt to assume their memory position again, but are prevented from doing so by the wall of the spherical recess 23, so that the quarters 36 will push against the wall of the spherical recess 23 with a considerable force. Thus, any movement of the spherical fixing portion 33 relative to the spherical recess 23 is prevented, so that the orientation of the coupling pin 30 relative to the transmucosal member 20 is fixed in the position set, at least in the case of such forces as may generally be exerted within the mouth. The fixing power can be increased by forming the spherical fixing portion 33 and/or the spherical recess 23 with a slightly rough surface.

It is observed that the combination of the coupling pin 30 and the transmucosal member 20 can thus be regarded as one integral part at temperatures above the critical temperature, and hence at least at such operating temperatures as may occur in the mouth. Thus, the invention makes it possible to implant an implantation pin in the jawbone in an orientation that is suitable for implantation, and to attach thereto a standard integral part comprising a coupling pin, while the coupling pin still has an orientation that is suitable for coupling with the dental-replacement member.

When setting the coupling pin 30 relative to the implantation pin 10, the dentist can work "by eye", but greater accuracy is achieved by means of the procedure to be described hereinafter with reference to FIG. 7, which is particularly preferable if a dental-replacement member is to be attached by means of a plurality of anchoring elements.

After implantation and ingrowth of the implantation pins 10, the gums 21 are opened locally and an auxiliary pin 50 is screwed into each implantation pin 10 by means of a comparatively long screw 51. Then, using an impression mass 52 which is known per se, an impression (negative) is made of the jaw and the auxiliary pins 50 protruding therefrom, as well as of any original dental elements (see FIG. 7A). This impression mass 52 is applied by means of a so-called "impression spoon" which is accessible from the side facing away from the jaw for unscrewing the screw 51, so that the impression mass 52 with the auxiliary pins 50 disposed therein can be removed (see FIG. 7B). Optionally, a temporary transmucosal member can then be attached to the implantation pins 10 to prevent closing of the gums.

Figure 7B:
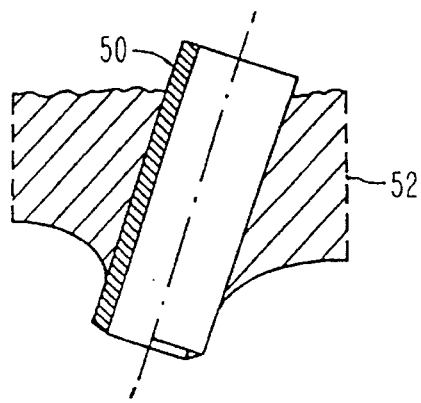
Figure 7C:
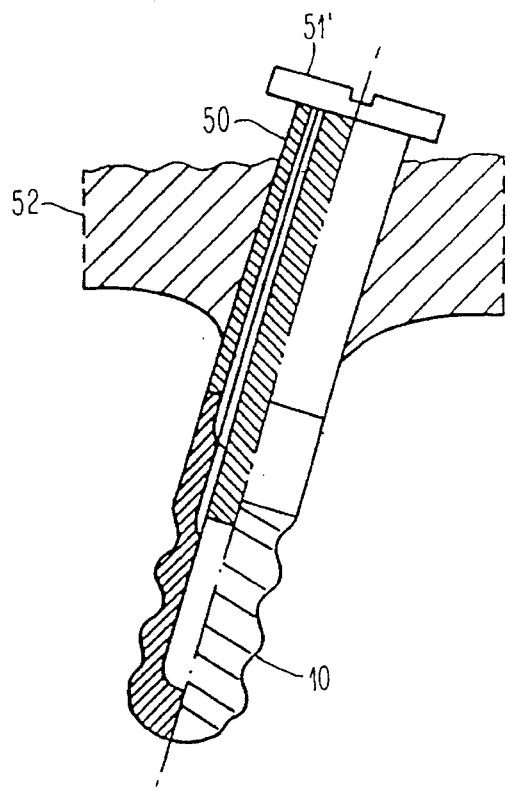
Figure 7D:
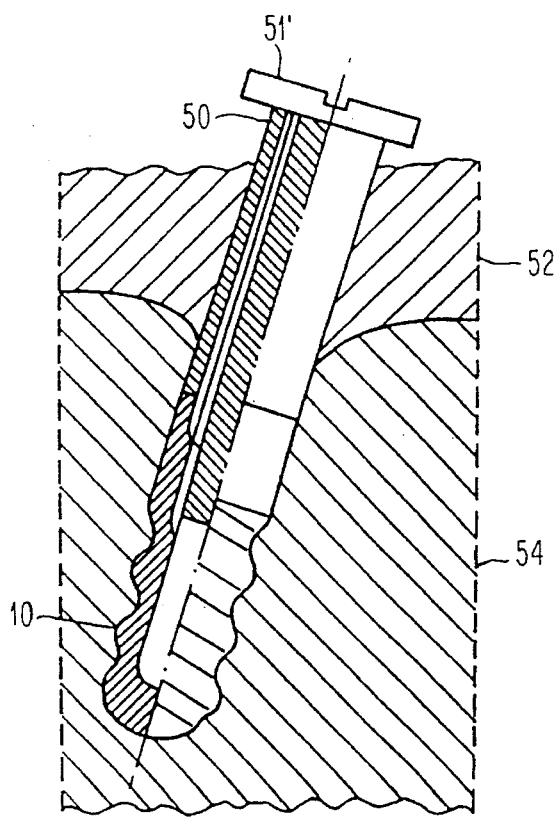
Figure 7E:
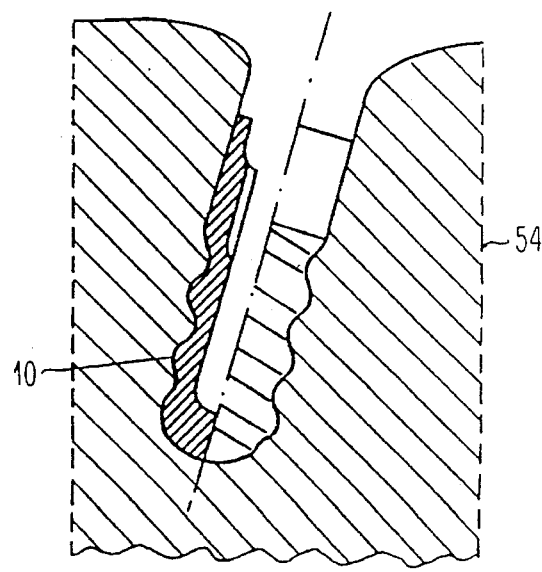
Figure 7G:
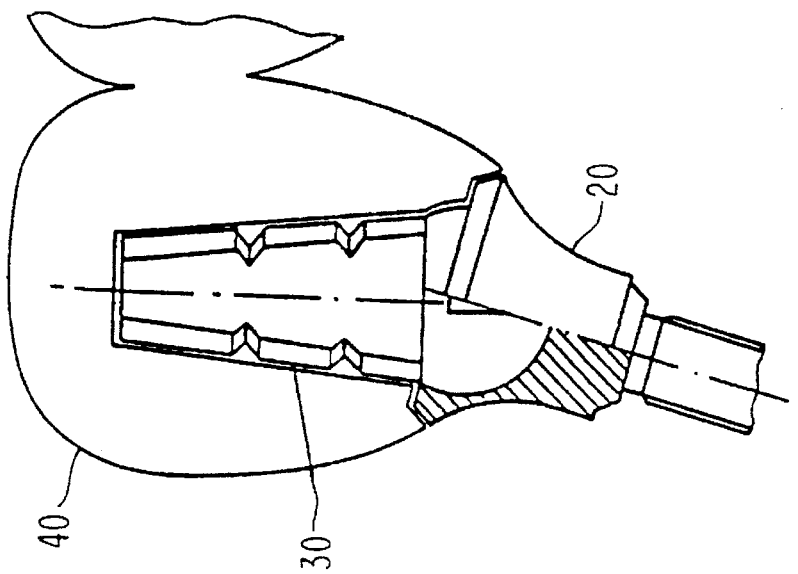

In a preferably separate laboratory, an implantation pin 10 is attached again to the auxiliary pins 50 stuck in the impression mass by means of a separate screw 51' (see FIG. 7C), and of the assembly an impression (positive) 54 is made (see FIG. 7D). This positive impression 54 (see FIG. 7E) is a replica of the relevant situation in the mouth, including the implantation pins 10.

Figure 7F:
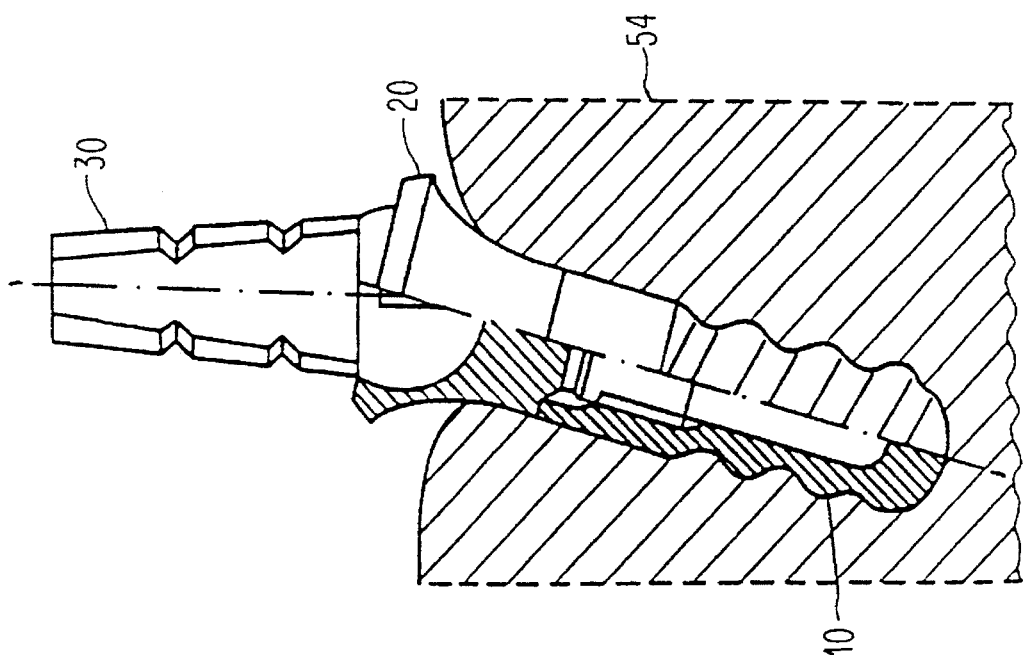

A respective combination of a transmucosal member 20 and a coupling pin 30 is mounted on these implantation pins, whereafter, after cooling appropriately, the coupling pins 30 are brought into a desired orientation and are secured in that desired orientation by heating (see FIG. 7F).

Then, recesses are provided in a dental-replacement member 40, which recesses correspond with the orientation of the coupling pins 30 of the positive impression 54. This may for instance be realized by moulding a wax model of the dental-replacement member 40 on the positive impression 54, and forming the dental-replacement member proper from the wax model by means of the lost-wax method, as is known per se.

The dental-replacement member 40 so prepared and the corresponding combinations of transmucosal member 20 and coupling pin 30 (see FIG. 7G) are fitted in the patient's mouth by the dentist, the dental-replacement member 40 generally fitting readily on the coupling pins 30 without friction or tension, when the abovementioned combinations of transmucosal member 20 and coupling pin 30 have been attached to the corresponding implantation pins 10.

Optionally, however, it is possible for the dentist to suspend the fixed position by locally cooling the coupling pins 30 and to fit the dental-replacement member over the coupling pins 30, whereby the pins 30 will orient themselves in the recesses 41 of the dental-replacement member. By reheating the coupling pins 30 again to a temperature above the critical temperature, the position of the coupling pins 30 thus adjusted to the dental-replacement member is maintained in the mouth. It will be clear that the surrounding parts, such as gums, are protected against the low temperature, for instance by means of a so-called cofferdam, as is known per se.

It will be clear that the invention also relates to embodiments in which the ball cup of the ball-and-socket joint consists of a memory material and in the memory position exerts an inwardly directed clamping force on the ball. In a possible embodiment, the transmucosal member 20 is made of memory material. However, since generally at least one slot is desired to provide clamping portions equivalent to the clamping portions 36, while, at the same time, such a slot is less desirable in conjunction with gums, the embodiment discussed above with reference to the drawing is preferred.

It will be clear to anyone skilled in the art that it is possible to change or modify the embodiment shown of the device according to the invention, without departing from the concept of the invention or the scope of protection.

We claim:

1. A device for attaching a member in replacement of part of a set of teeth, comprising:
   a hollow implantation pin to be implanted in a jawbone; and
   a coupling pin adapted to be rigidly attached to the hollow implantation pin by means of and further comprises a ball-and-socket joint; wherein:
   a coupling part of the ball-and-socket joint is at least partly made of a memory material to prevent pivotal motion of the ball-and-socket joint at an operating temperature.

2. A device according to claim 1, wherein the coupling pin comprises at one end a fixing portion substantially shaped as a segment of a sphere, which segment of a sphere is entirely made of memory material.

3. A device according to claim 2, wherein the coupling pin is entirely made of memory material.

4. A device according to claim 1, wherein the coupling part of the ball-and-socket joint that is at least partly made of memory material is subdivided into separate clamping parts by means of slots.

5. A device according to claim 4, wherein two slots are provided in said coupling part in substantially perpendicular relation relative to each other.

6. A device according to claim 1, wherein the surface of said coupling part of the ball-and-socket joint is slightly roughened.

7. A device according to claim 1, wherein said ball-and-socket joint further comprises a transmucosal member, said transmucosal member being suitable at one end thereof for attachment to the hollow implantation pin and at its other end comprises a second coupling part of the ball-and-socket joint.

8. A device according to claim 1, wherein a critical temperature of the memory material is lower than 37° C.

9. A device according to claim 8, wherein the critical temperature of the memory material is about 0° C.

10. A device according to claim 1, wherein the memory material is nitinol.

11. A coupling pin for attaching a replacement part of a set of teeth to an implantation pin, said coupling pin comprising a coupling part of a ball-and-socket joint at an end of said pin wherein said coupling part is at least partly made of a memory material.

12. A coupling pin according to claim 11, wherein the coupling pin comprises at one end a fixing portion, substantially shaped as a segment of a sphere, said segment of a sphere being entirely made of memory material.

13. A coupling pin according to claim 12, wherein the coupling pin is entirely made of memory material.

14. A coupling pin according to claim 11, wherein the coupling part of the ball-and socket joint is subdivided into separate clamping parts by slots.

15. A coupling pin according to claim 14, wherein two slots are provided in said coupling part in substantially perpendicular relation to each other.

16. A coupling pin according to claim 11 further comprising a transmucosal member, which transmucosal member is suitable at one end thereof for attachment to the implantation pin and at its other end comprises a coupling part of said ball-and-socket joint.

17. A transmucosal member for attaching a replacement part of a set of teeth to an implantation pin, said transmucosal member comprising a first end and a second end, said first end comprising a means for attaching the transmucosal member to the implantation pin and said second end comprising a coupling part of a ball-and-socket joint, wherein said coupling part is at least partly made of memory material.

18. A transmucosal member according to claim 17 further comprising a coupling pin, which coupling pin is suitable at one end thereof for attachment to the replacement member and at its other end comprises a coupling part of said ball-and-socket joint.

19. A method for attaching a member in replacement of part of a set of teeth, in which a coupling pin is attached, to the member by means of a corresponding recess in the member and the coupling pin is further attached to a ball-and-socket joint which in turn, is attached to an implantation pin implanted in a jawbone, wherein at least one of the coupling parts of the ball-and-socket joint is made of a memory material, said method comprising the steps of:
   cooling at least the part of the ball-and-socket joint that is made of memory material to a temperature below a critical temperature to make the ball-and-socket joint pivotable;
   positioning the ball-and-socket joint so as to bring the coupling pin into a desired orientation relative to the implantation pin; and
   heating at least the part of the ball-and-socket joint that is made of memory material to a temperature above the critical temperature so as to fix the desired position of the ball-and-socket joint.

20. A method according to claim 19, wherein the steps of cooling, positioning and heating are carried out after the coupling pin has been attached to the implantation pin.

* * * * *